(12) United States Patent
Tapper et al.

(10) Patent No.: US 9,440,092 B2
(45) Date of Patent: *Sep. 13, 2016

(54) LIGHT THERAPY PLATFORM SYSTEM

(71) Applicant: Johnson & Johnson Consumer Inc., Skillman, NJ (US)

(72) Inventors: Jay Tapper, Wayne, PA (US); Lawrence A Blaustein, Chagrin Falls, OH (US); David Shuter, Palm Beach Gardens, FL (US); Eric Freitag, Brooklyn, NY (US); Charles Peter Althoff, New York, NY (US); Alistair Douglas Bramley, Brooklyn, NY (US); Daniel Joseph Shuter, Palm Beach Gardens, FL (US); Zbigniew Paul Lorenc, New York, NY (US); Allen Zadeh, Brooklyn, NY (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/688,332

(22) Filed: Apr. 16, 2015

(65) Prior Publication Data

US 2015/0224336 A1 Aug. 13, 2015

Related U.S. Application Data

(60) Continuation of application No. 14/324,453, filed on Jul. 7, 2014, which is a division of application No. 13/604,012, filed on Sep. 5, 2012, now Pat. No. 8,771,328.

(60) Provisional application No. 61/532,140, filed on Sep. 8, 2011.

(51) Int. Cl.
*A61N 5/06* (2006.01)
*A61F 9/04* (2006.01)
(Continued)

(52) U.S. Cl.
CPC ............. *A61N 5/0616* (2013.01); *A61F 9/045* (2013.01); *A61B 2017/00057* (2013.01);
(Continued)

(58) Field of Classification Search
CPC ............ G02C 9/00; A61N 1/39; A61N 1/00; A61M 21/00; A61B 18/18; F21V 5/00
USPC ........ 351/47; 607/88, 89; 600/15, 27; 606/9; 362/327
See application file for complete search history.

(56) References Cited

U.S. PATENT DOCUMENTS

| 1,626,617 A | 5/1927 | Last |
| 1,692,669 A | 11/1928 | Last |

(Continued)

FOREIGN PATENT DOCUMENTS

| DE | 20 20009 000 891 U1 | 7/2009 |
| EP | 1 074 275 A1 | 2/2001 |

(Continued)

OTHER PUBLICATIONS

PCT/US12/53838 International Search Report, mailed Jan. 24, 2013.
(Continued)

*Primary Examiner* — William Thomson
*Assistant Examiner* — Victor Shapiro
(74) *Attorney, Agent, or Firm* — Fay Sharpe LLP

(57) ABSTRACT

Phototherapy systems comprising a therapeutic lamp platform for radiant lamps such as LEDs disposed in an assembly including a reflective surface facing towards a patient and a plurality of light apertures substantially aligned with the LEDs for communicating lamp radiation from the lamps to a user. The lamps and associated circuitry are disposed so that the reflective surface is relatively smooth and seamless towards the patient. The walls have a malleable rigidity for flexible adjustability relative to the user, and the device is mounted to the user with a frame.

18 Claims, 14 Drawing Sheets

(51) Int. Cl.
    *A61B 17/00* (2006.01)
    *A61B 18/00* (2006.01)
    *A61N 5/067* (2006.01)

(52) U.S. Cl.
    CPC .............. *A61B 2018/00642* (2013.01); *A61B 2018/00791* (2013.01); *A61B 2018/00988* (2013.01); *A61B 2090/049* (2016.02); *A61N 2005/067* (2013.01); *A61N 2005/0626* (2013.01); *A61N 2005/0627* (2013.01); *A61N 2005/0628* (2013.01); *A61N 2005/0645* (2013.01); *A61N 2005/0647* (2013.01); *A61N 2005/0648* (2013.01); *A61N 2005/0652* (2013.01); *A61N 2005/0654* (2013.01); *A61N 2005/0659* (2013.01); *A61N 2005/0663* (2013.01); *A61N 2005/0666* (2013.01)

(56) References Cited

U.S. PATENT DOCUMENTS

| | | |
|---|---|---|
| 3,279,468 A | 10/1966 | Le Vine |
| 3,376,870 A | 4/1968 | Yamamoto et al. |
| 3,971,387 A | 7/1976 | Mantell |
| 5,085,227 A | 2/1992 | Ramon |
| 5,616,140 A | 4/1997 | Prescott |
| 5,824,023 A | 10/1998 | Anderson |
| 5,913,883 A | 6/1999 | Alexander et al. |
| 6,045,575 A | 4/2000 | Rosen et al. |
| 6,290,713 B1 | 9/2001 | Russell |
| 6,293,900 B1 | 9/2001 | Bove et al. |
| 6,443,978 B1 | 9/2002 | Zharov |
| 6,471,716 B1 | 10/2002 | Pecukonis |
| 6,508,813 B1 | 1/2003 | Altshuler |
| 6,511,475 B1 | 1/2003 | Altshuler et al. |
| 6,517,532 B1 | 2/2003 | Altshuler et al. |
| 7,125,416 B2 | 10/2006 | Kent et al. |
| 7,222,995 B1 | 5/2007 | Bayat et al. |
| 7,520,630 B2 | 4/2009 | Murphy |
| 8,192,473 B2 | 6/2012 | Tucker et al. |
| 8,252,033 B2 | 8/2012 | Tucker et al. |
| 8,771,328 B2 | 7/2014 | Tapper et al. |
| 8,858,607 B1 | 10/2014 | Jones |
| 2004/0162549 A1 | 8/2004 | Altshuler |
| 2005/0070977 A1 | 3/2005 | Molina |
| 2005/0080465 A1 | 4/2005 | Zelickson et al. |
| 2005/0278003 A1 | 12/2005 | Feldman |
| 2006/0030908 A1 | 2/2006 | Powell et al. |
| 2006/0217690 A1 | 9/2006 | Bastin et al. |
| 2006/0217787 A1 | 9/2006 | Olson et al. |
| 2006/0268220 A1 | 11/2006 | Hogan |
| 2007/0156208 A1 | 7/2007 | Havell et al. |
| 2007/0208395 A1 | 9/2007 | Leclerc et al. |
| 2007/0233208 A1 | 10/2007 | Kurtz et al. |
| 2008/0065056 A1 | 3/2008 | Powell et al. |
| 2008/0269849 A1 | 10/2008 | Lewis |
| 2009/0143842 A1 | 6/2009 | Cumbie et al. |
| 2010/0069898 A1 | 3/2010 | O'Neil et al. |
| 2010/0121419 A1 | 5/2010 | Douglas |
| 2011/0015707 A1 | 1/2011 | Tucker et al. |
| 2011/0040355 A1 | 2/2011 | Francis |
| 2011/0160814 A2 | 6/2011 | Tucker et al. |
| 2011/0257467 A1 | 10/2011 | Clegg et al. |

FOREIGN PATENT DOCUMENTS

| | | |
|---|---|---|
| EP | 1 916 016 A1 | 4/2008 |
| GB | 2 380 134 A | 4/2003 |
| WO | WO 2006/028461 A2 | 3/2006 |
| WO | WO 2010/076707 A1 | 7/2010 |

OTHER PUBLICATIONS

PCT/US14/69789 International Search Report, mailed Mar. 13, 2015.

European Search Report for EP Patent Application 12 830 671.9 dated May 6, 2015.

PCT/US2014/069789—PCT Notification Concerning Transmittal of Int'l Preliminary Report on Patentability dated Jun. 23, 2016 (Johnson & Johnson Consumer, Inc.).

LIGHT THERAPY PLATFORM SYSTEM

This application claims the priority benefit of U.S. application Ser. No. 61/532,140, filed Sep. 8, 2011, the disclosure of which is incorporated herein by reference.

FIELD

The present embodiments relate to devices and methods for delivering light-based skin therapy treatments for improving skin health, such as anti-aging enhancement or acne prevention, using light-emitting diode (LED) light therapy, although other types of light radiating sources can be used.

BACKGROUND

Certain light spectrums emitted by LEDs (blue or red) are known to be therapeutic for skin treatment against maladies such as acne, or are beneficial to inhibit skin aging. However, there is a need to provide users/patients with a convenient at-home light therapy delivery device such as a wearable mask, veil or hood that is adjustable or flexible to conform to different sizes and shapes, and that is simple to use without user discomfort. Currently available at-home, consumer usable products on the market are fixed to one-size and/or usually have to be hand-held; which generally have not proven satisfactory for providing the best or desired light dispersion. The alternative is customers visiting a doctor's office to receive treatments.

Prior known light therapy devices, particularly masks, have suffered from problems relating to the exposure of the LEDs and the associated circuitry to power the LEDs to contact by users. More particularly, in an effort to maximize light communication to a patient, the LEDs have been disposed in a manner which allow them to be physically engaged (e.g., touched) by a patient, or even contact a treatment surface, which processes are debilitating to the LEDs as a result of the accumulation of dirt and oil. In addition, any such engagement can be dangerous to patients who are exposed to the sharp or hot edges of the LEDs and the associated circuitry. The exposure of detailed circuitry presents an intimidating and unpleasant experience when the therapy requires several minutes of time for completion and the mask is disposed relatively close to the face, often causing an uncomfortable, claustrophobic sensation over time to the patient.

A hands-free therapeutic experience is always better than having to hold the device in a particular position for extended periods of time during the therapy. Numerous assemblies have been conceived for mounting masks and helmet-like devices to varieties of straps, bands, wraps and cords, which can result in a pressing of the support and mounting assembly closely against the hair or scalp of a patient. There is always a need to minimize the extent of such attachment assemblies so that on the one hand the subject device is securely attached on the patient, but also that the attaching structure has minimal consequence to the patient's comfort during the therapy itself. Being relatively light in weight, and easily and minimally supported during therapeutic use are important to consumer acceptance.

As users come in a variety of shapes and sizes, devices should be size or area adjustable so that the therapy can be efficiently applied and/or selectively intensified to desired treatment areas.

Lastly, particularly in therapeutic devices treating facial areas, eye protection is needed to avoid light damage or irritation to a patient's eyes. Prior known devices have typically used separable patches which must rest on the eye area to block the therapeutic light from communication to the eye system itself. There is a need for a better way that is readily adaptable to communicate therapeutic light to areas near the eyes, particularly with regard to anti-aging treatments, and still protect the patient.

It is desired to provide alternative means of using the benefits of the light therapy in a manner to maximize therapeutic efficiencies in exposure while maintaining ease and convenience of use. For this reason, a variety of light weight, flexible and adjustable embodiments are disclosed within this disclosure incorporating a variety of energy varying applications responsive to user conditions or needs.

SUMMARY

The present embodiments comprise phototherapy systems and devices comprising a therapeutic lamp platform for radiant lamps such as LEDs are disposed in an assembly comprising a first wall to which the lamps are affixed thereto and a second wall, closer to the patient, spaced from the first wall wherein the lamps are recessed relative thereto. The second wall comprises a reflective surface facing towards a patient and a plurality of light apertures substantially aligned with the LEDs on the first wall for communicating lamp radiation from the lamps to a user. The lamps and associated circuitry are disposed between the first and second wall so that the reflective surface is relatively smooth and seamless towards the patient. The number of lamps are minimized, as is the circuitry therefor, and other assembly materials are purposefully selected for a relatively light weight assembly resulting in enhanced user comfort during therapy sessions. The walls have a malleable rigidity for flexible adjustability relative to the user. More particularly, the walls have a concave configuration relative to the face of the user which is adjustable relative to a rest position to be expandable relative to a size of the head of the user for a close fitting and secure engagement to the user during use. The device is mounted to the user with a frame comprising an eyeglass frame or goggles including lenses for shielding the user's eyes from lamp radiation. The adjustability of the embodiments is further enhanced by the walls being pivotable relative to the support frame and where the frames may include telescopic temple arms for selective adjustability relative to the head size of the user. The device is thus supported on the patient as a wearable hands-free mask or the like. A power source communicates energy to the lamps and comprises a remote battery pack and may also include a control processor for counting the number of uses by the device for the user and for indicating a need for device replacement after a predetermined number of uses.

The present embodiments comprise an adjustable/flexible platform for providing a light-based therapy that is adaptable to the user's receptive surfaces, whether based on size or condition, wherein the light therapy can be applied without limitation of the kind of light and without limitation of the ultimate purpose of the therapy, i.e., beauty, health, and/or wound healing. Such sources can vary in the form of the radiant energy delivery. Pulsed light (IPL), focused light (lasers) and other methods of manipulating light energy are encompassed within the present embodiments. Other methods of light emission may comprise continuous, pulsed, focused, diffuse, multi wavelength, single wavelength, visible and/or non-visible light wavelengths.

A present embodiment describes forms such as a shaped/fitted mask, goggles, eye mask, shroud or hood, and facial mask (collectively referred to as "mask") with LED light emitted from LED bulbs or LED strips that are capable of being adjusted to accommodate the variances in face size or areas intended for therapeutic attention. Control systems are included to vary light intensity, frequency or direction.

The platform can be secured to the head by multiple means: eyeglass frames, straps, drawstring, harness, velcro, turn dial or snap and buttons. As the mask is secured it can be adjusted upward, for chin to forehead coverage. It can also be adjusted outward, for side-to-side coverage. In addition, once the platform has been bent/slid to cover the face area, the distance of the platform from the skin can be adjusted for achieving a desired light intensity relative to a user's skin surface. Thus, the light therapy can be maximized in up to three physical dimensions.

The subject adjustability may be implemented through "smart" processing and sensor systems for enhanced flexibility/adjustability in the form of adjustable energy output, adjustable wavelengths, priority zones, timers, and the like. The sensors of the sensor systems will enable the subject embodiments to have the ability to evaluate the skin of the face and body of a patient with sensors for color, wrinkles, age spots, acne, lesion density, and the like, and plan a smart treatment, utilizing more or less energy on the priority zones. The subject embodiments can be smart from the standpoint of skin type, age, overall severity of problems and have the ability to customize the treatment accordingly.

In yet another embodiment, the lamps are embedded in a flexible sheet of formable material and are integrally molded as strips within a material sheet.

In addition, control systems can measure or count device usage and communicate historical usage, and indicate a time for replacement.

The present disclosure thus describes a fully flexible and adjustable LED device which provides improved usability and light dispersion.

DETAILED DESCRIPTION

Figure 1:
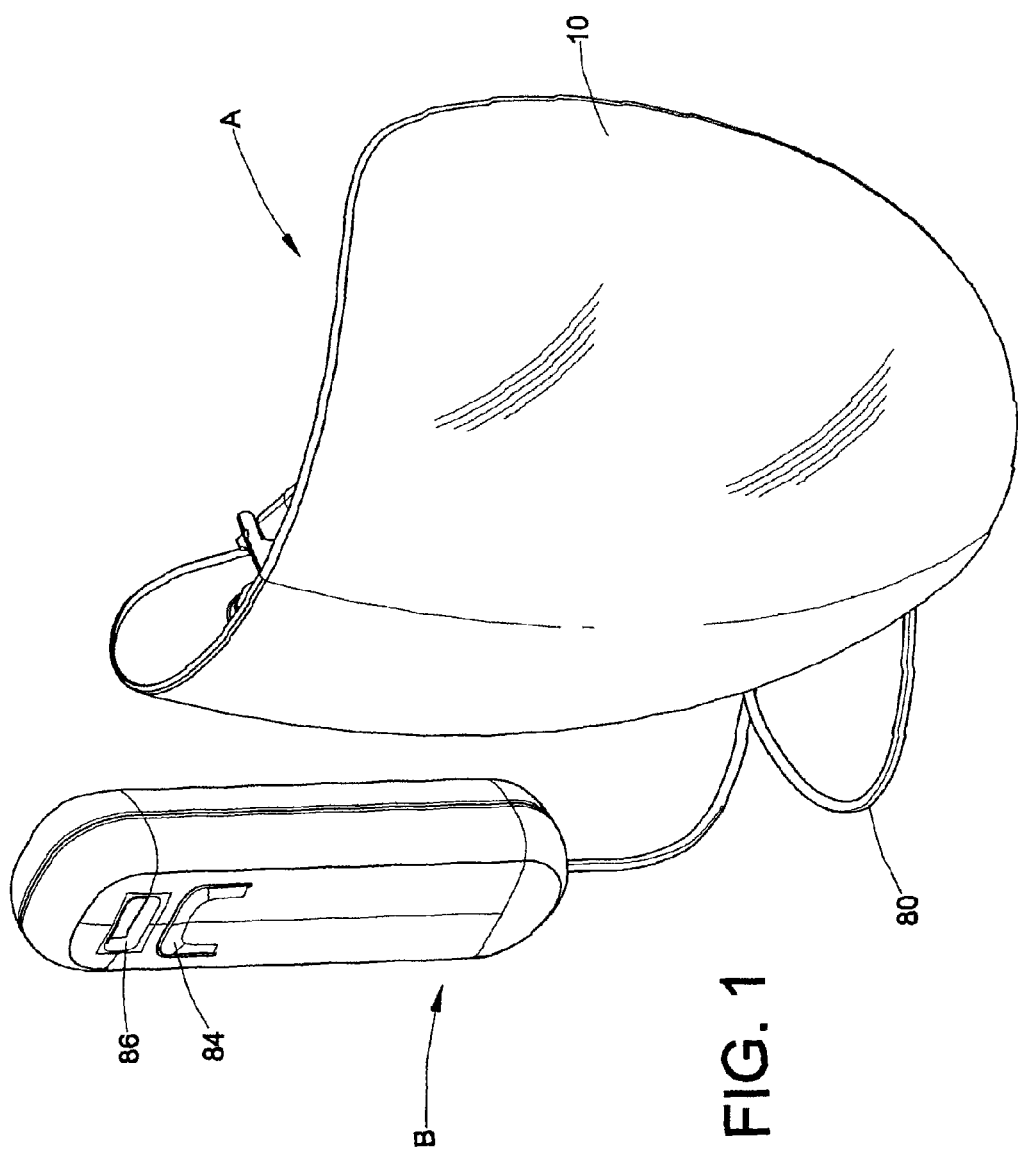
FIG. 1 is a perspective view of one embodiment of a therapeutic lamp platform comprising a wearable mask.

The subject embodiments relate to a phototherapy system including methods and devices, preferably comprising a wearable hands-free device with a remote battery pack for powering therapeutic lamps in the device. The subject devices display numerous benefits including a light platform wherein the platform and the lamps therein are properly positionable relative to a user during use with no human touch. That is, structural componentry of the device not only supports the lamp platform on the user, but functions as a guide for the appropriate disposition of the lamps relative to the treatment areas of the user. The structural assembly of the device precludes sharp or hot surfaces from being engageable by a user as the lamps are recessed relative to an inner reflective surface closest to and facing the patient treatment surface. Circuit componentry to communicate power to the lamps is also encased within the wall structure. Therapeutic light, shining through wall apertures, is communicated to the user while the lamps and the circuitry are effectively encased within the spaced wall structure. A smooth seamless surface is thus presented to the user that is properly spaced for the desired therapeutic treatments, yet provides improved ventilation so that an aesthetic and appealing device surface is presented to the user that minimizes user discomfort. Other benefits relate to the adjustability of the device in the form of a flexible mask which forms upon user receipt to match a treatment surface, e.g., a head size, of the user. Smart componentry not only measures device usage, but may also calculate lamp degradations so that a time for proper replacement can be communicated to a user. The overall assembly is purposefully constructed of relatively light weight and minimized componentry for ease of user use and comfort.

More particularly, and with reference to FIGS. 1-4, subject embodiments preferably comprise a lamp platform A and a remote battery pack B. The platform A is comprised of a wall structure 10 encasing the plurality of therapeutic lamps such as red and blue LEDs 12 and circuitry 14 for communicating power to the lamps via cable 80 and connector 83 from the battery pack B. Other radiant energy forms could also include fluorescents, lasers or infrareds. The wall structure 10 is mounted on a support frame 20 connected via snap-out pivotal connections 22 which allows the wall structure to adjust position via a slight pivot relative to the frame 20. The frame 20 also includes protective lenses 24 and a nose bridge 26. The temple arms 28 may be fixed or telescopic and hinge relative to the frame 20 so that the platform A can be mounted on a user in a hands-free support manner via resting on the nose with the nose bridge 26 and the ears with temple arms 28.

Figure 3:
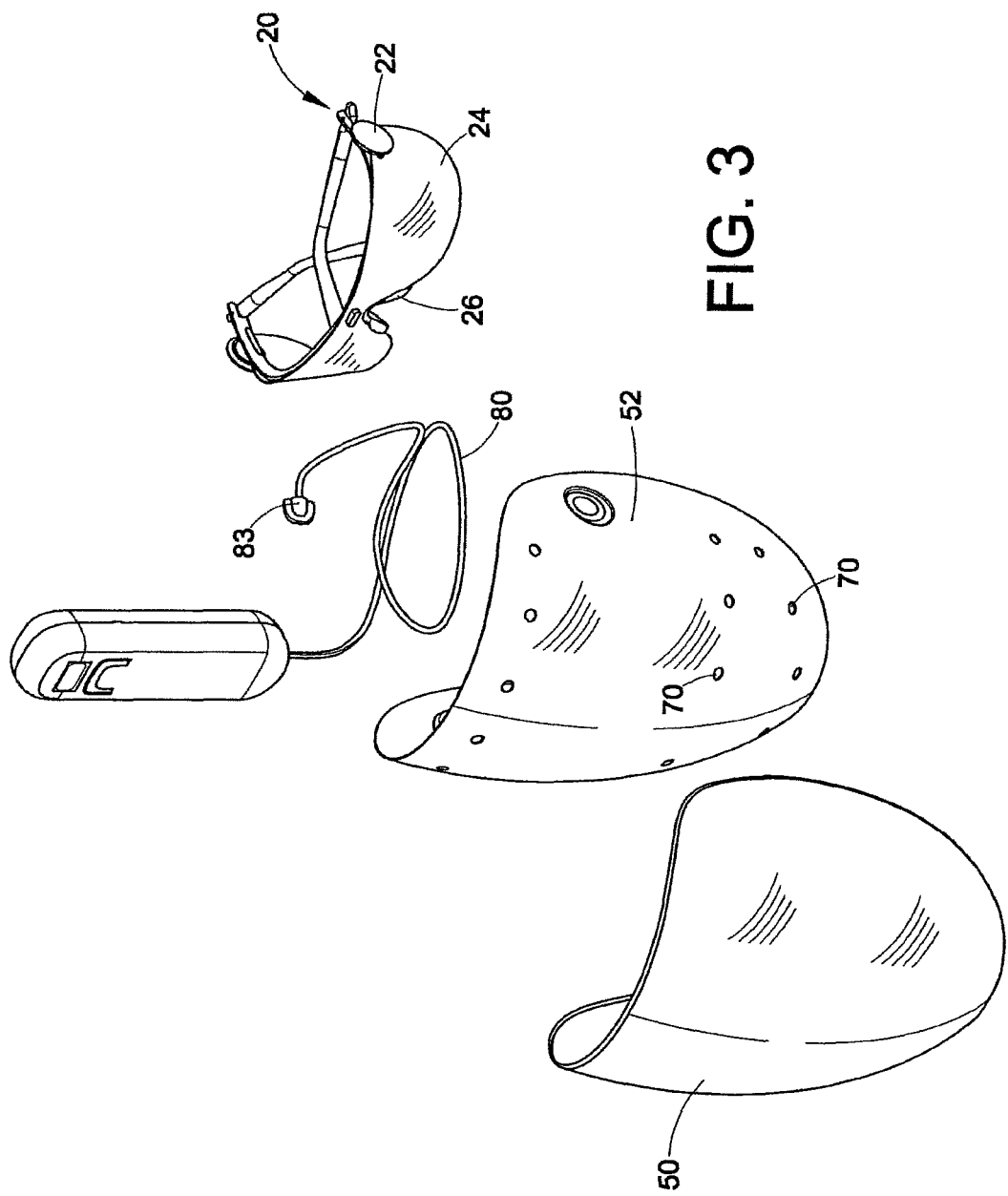
FIG. 3 is an exploded perspective view of FIG. 1.
Figure 4:
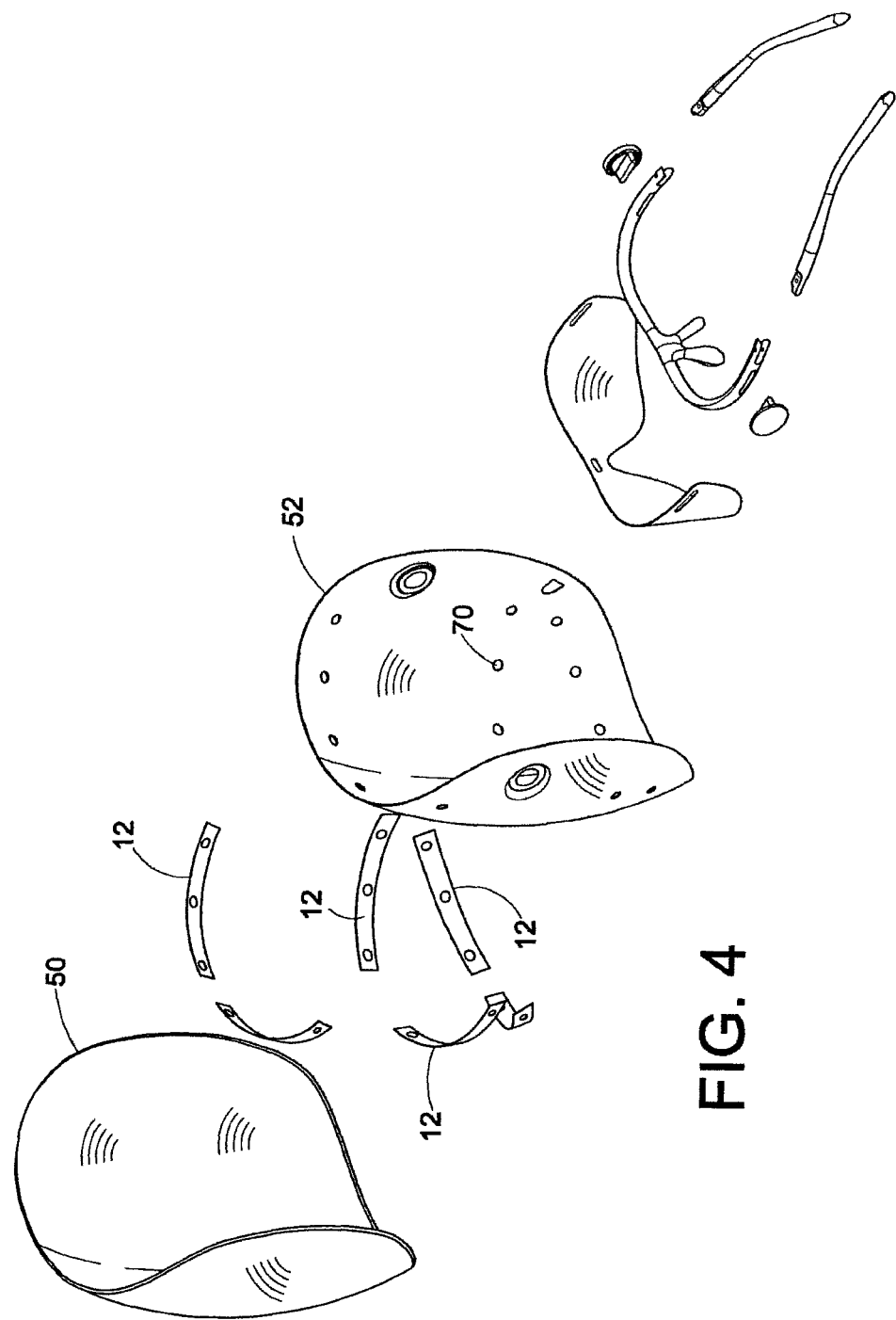
FIG. 4 is an exploded perspective view of FIG. 2.

With reference to FIGS. 3, 4, 6, 7 and 8 it can be seen that the wall structure 10 is comprised of an outer wall 50 and an inner wall 52. The outer wall is disposed furthest away from the treatment surface of the user, while the inner wall 52 is disposed closer thereto. The walls have a concave configuration in both horizontal and vertical directions and are constructed of a plastic material having a malleable rigidity so that the structure 10 can be bent and deflected slightly during use. The concavity comprises a multi-dimensional parabolic curvature for catching and reflecting the radiation back to the treatment areas. It is intended that the concavity is slightly smaller than the head of the user so that the mask has to be bent out when applied thereby providing a close but comfortable tightness on the user which will keep the assembly A in a desired position during use. The concavity also positions the therapeutic lamps or LEDs 12 in desired positions relative to the user. The spacing 54 between walls 50 and 52 receives the lamps 12 and circuitry 14 so that the lamps and circuitry are interposed between the walls for enhanced safety and convenience purposes. It can be seen that the spacing is diminished from the middle of the device towards the end portions 58, 60; however, the entire end perimeter of the assembly 10 is sealed as the walls come together. Such a mating seal is typically effected through a sonic weld arrangement. Alternatively, local sealing points (not shown) can be employed to assemble the walls together with spaced intermediate seals. Thus, the inner and outer masks have different radii of concavity but present an integral structure as far as the user is concerned. The outer wall 50 primarily functions as a support for the lamps 12 and circuitry 14. With reference to FIG. 4 it can be seen that the lamps are disposed on the wall 50 in a predetermined manner for radiating treatment areas most susceptible for the phototherapeutic treatment. A minimum number of lamps 12 are intended but still enough to provide effective therapy. Alternatively, the lamps could be fixed to the inner wall 52. Regardless of which wall supports the lamps, the lamps need to be properly aligned with apertures 70 to desired treatment areas.

Rather than placing a plurality of LEDs randomly, the subject LEDs are specifically minimized in number and disposed relative to the treatment areas and wall parabolic reflectivity to effect the desired therapy. More particularly, it can be seen that the individual lamps 12, and associated inner wall apertures 70, are disposed to treat the most common areas benefiting from the therapy. The present embodiments illustrate a placement pattern useful for skin acne treatment. Other placement patterns are certainly intended to fall within the scope of the disclosed embodiments. Here three LED strips are seen and would typically comprise two blue strips on the top and bottom of a middle red strip, as these frequencies are most useful for acne treatment. The subject invention may include only blue, only red, or any other mixed combination of LED or other radiant energy form pattern. The illustrated pattern would thus have intensified therapeutic effect on the jaw line, chin, cheek and forehead, but not the eyelids. Light sources can include LEDs, fluorescents, lasers or infrareds as an example. Such sources can vary in the form of the radiant energy delivery. Pulsed light (IPL), focused light (lasers) and other methods of manipulating light energy are encompassed within the present embodiments. Other methods of light emission may comprise continuous, pulsed, focused, diffuse, multi wavelength, single wavelength, visible and/or non-visible light wavelengths.

The inner wall 52 is comprised of a smooth seamless reflective surface facing the treatment area and includes a plurality of apertures 70 matingly aligned relative to the lamps so that the lamps can radiate the therapeutic light through the apertures 70. Accordingly, the LEDs 12 are recessed relative to the inner wall 52 to preclude contact with the treatment surface and to make it very difficult for the lamps themselves to be in any way contacted by the user. Such an assembly results in a controlled communication of radiating therapy in a manner to impart a predetermined cone of therapeutic light on to a treatment area. The apertures are disposed relative to desired treatment areas and wall parabolic configuration for even light distributions across the treatment area. A combination of such a controlled cone of light, predetermined disposition of the lamps themselves on the platform, an inner reflective surface on the inner wall 52, and a controlled positioning of the assembly relative to the treatment area via a platform position relative to contact areas of the nose and the ears, presents an assembly which presents a highly predictable distributive pattern of the light (predetermined cones of light per light source), thereby minimizing the number of lamps 12 that need to be included for effective treatment.

Figure 2:
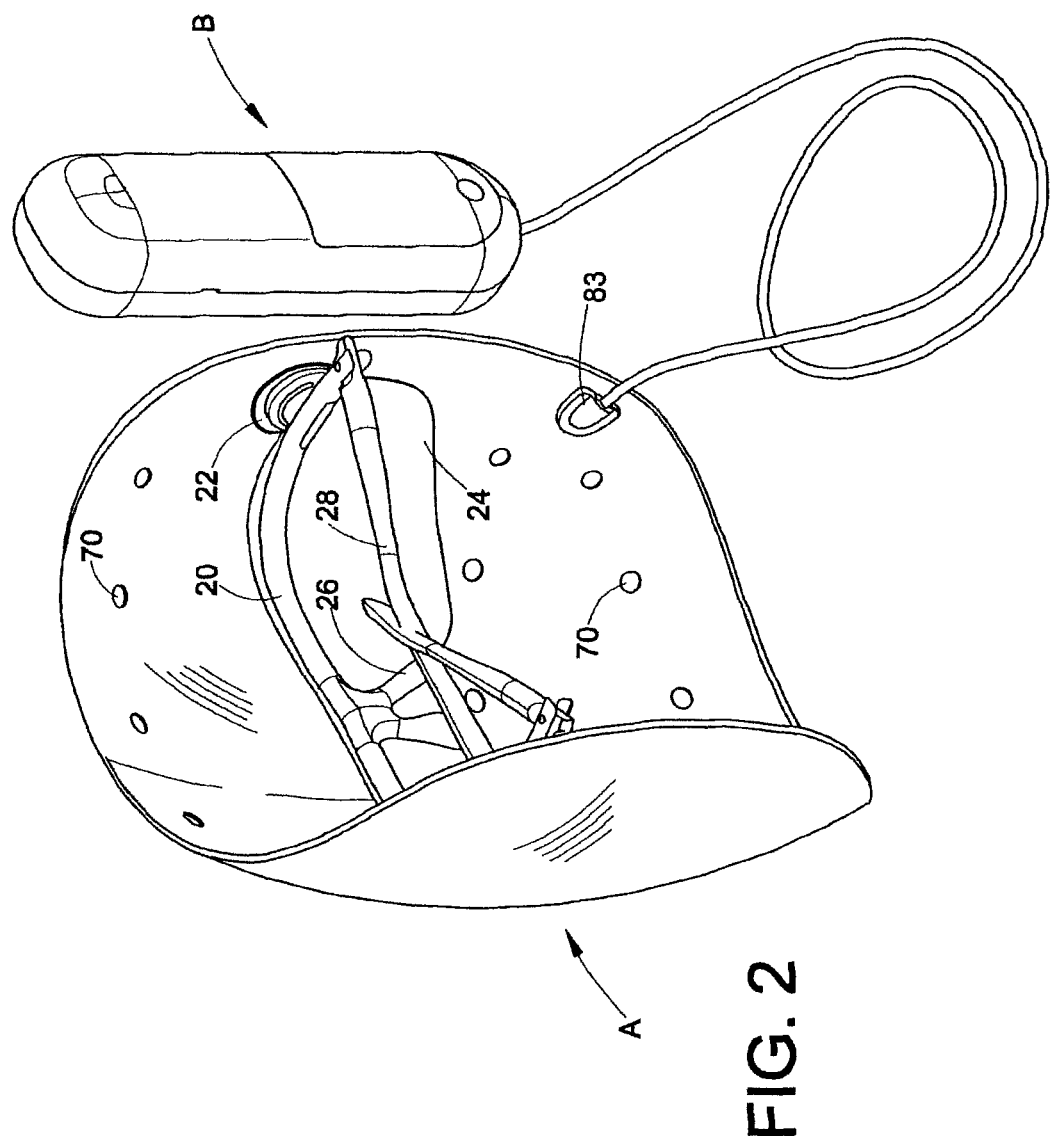
FIG. 2 is another perspective view of the device of FIG. 1.

With reference to FIGS. 2, 3 and 4, one embodiment comprises a support frame essentially comprising eyeglass frames as the associated support structure for the platform 10. Interchangeable lenses 24 can be used to adjust the level of protection afforded by the lenses or their relative shape. Although not shown therein, telescopic temple arms 28 may telescope for better sizing relative to the head size of the user. Formable ear latches can also be included as part of the temple arms. Alternatively, the arms could include a head strap. The pivotable joints 22 allow the wall structure to pivot relative to the frames so that a user may adjust light intensity relative to a treatment area by moving the layers closer or farther away. As noted above, the platform 10 is flexible with a concave parabolic bias, but still has a malleable rigidity. When the frame 10 is received on the user, it is disposed to expand the platform parabolic bias to form a match to the size of the user. Eyeglass frame reference contact points of the user may comprise the nasion area, the nose bridge and the ears of the user. Alternatively, the support frame can comprise a goggle and head strap configuration relying on the nasion area.

Figure 5:
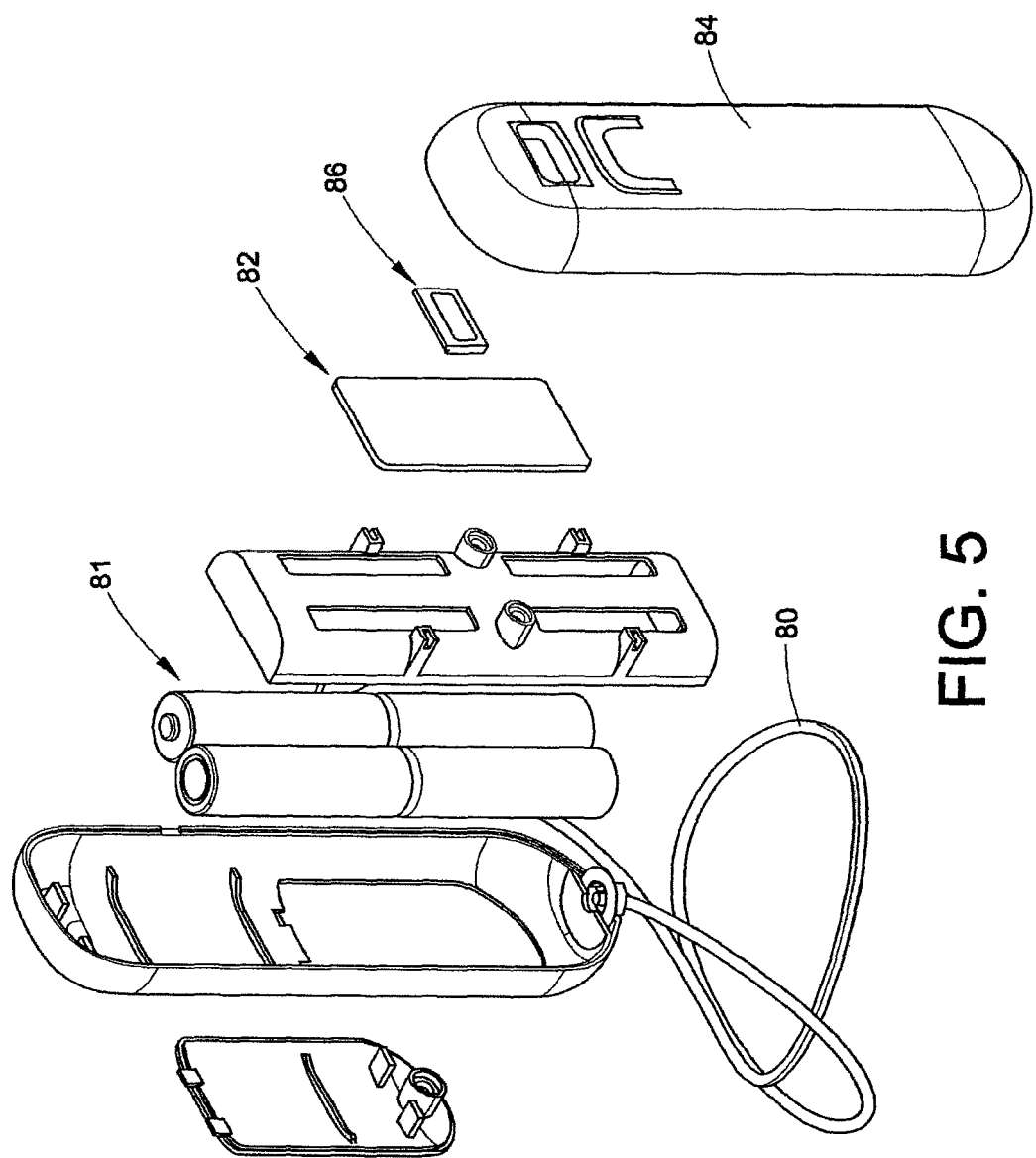
FIG. 5 is an exploded perspective view of the controller B.
Figure 6:
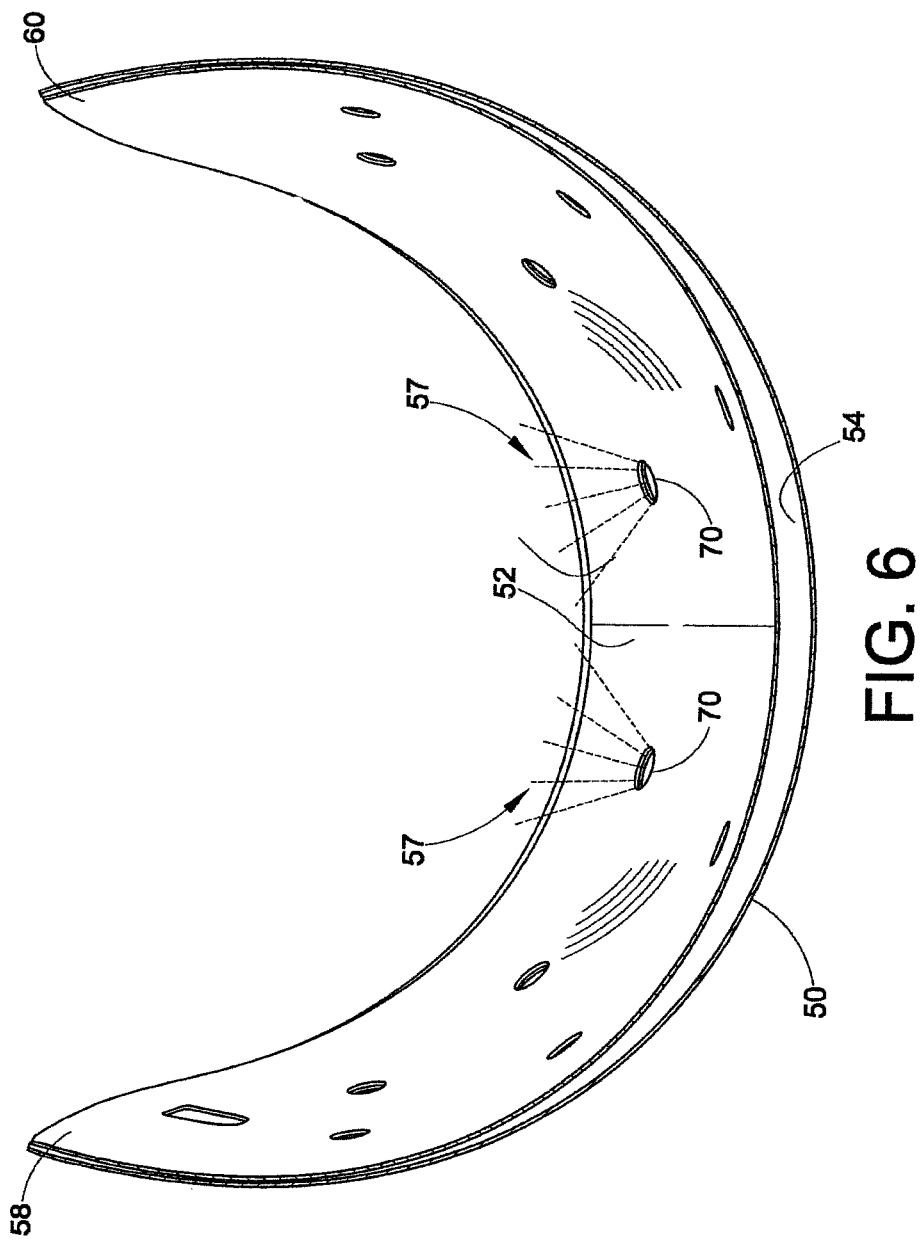
FIG. 6 is a cross-sectional view showing a two-wall structure of the embodiment of FIG. 1 wherein an inner wall includes light apertures aligned with the LEDs for communicating the therapeutic light to the user.
Figure 7:
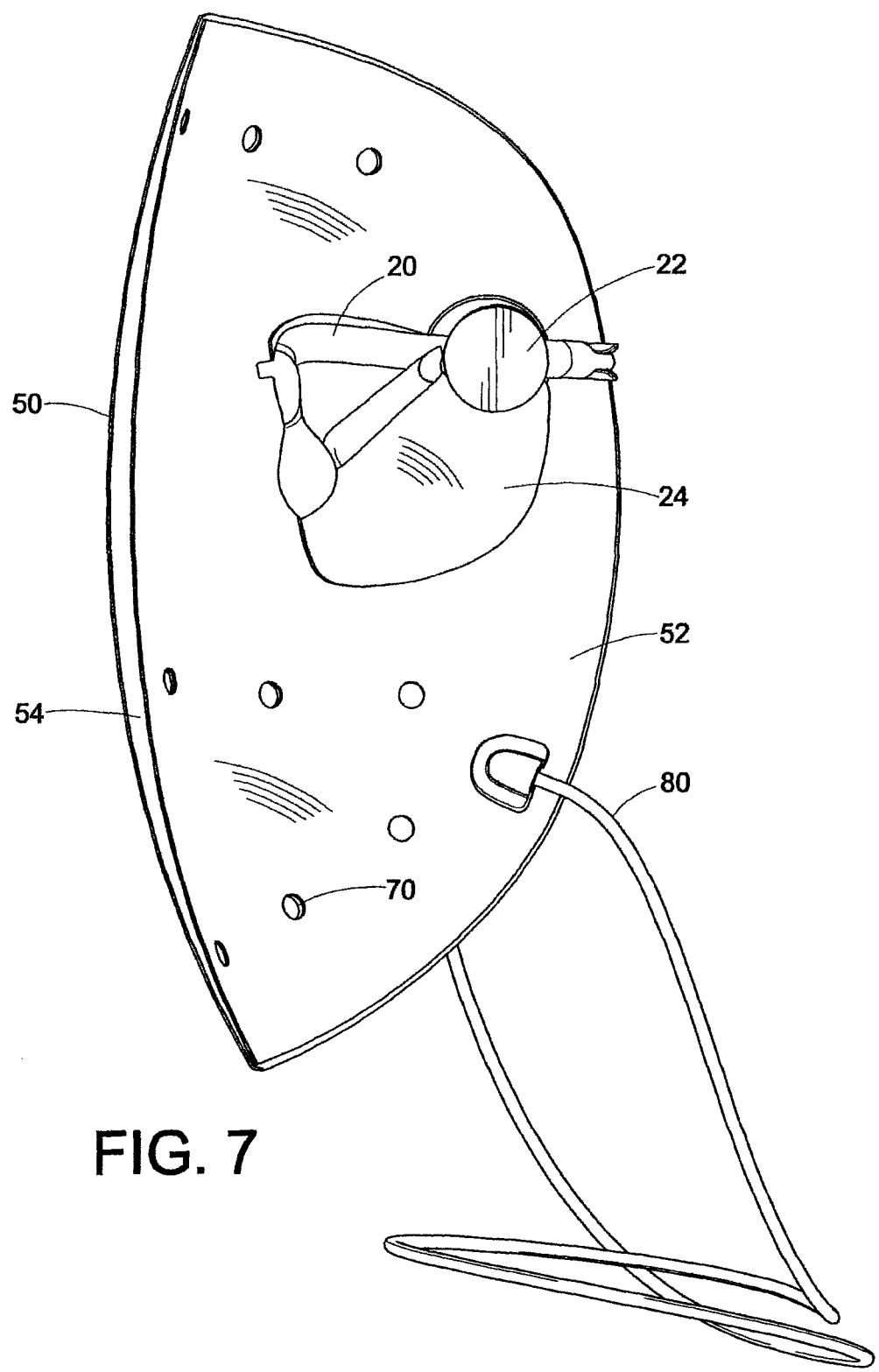
FIG. 7 is a second cross-sectional view taken along a vertical center-line.
Figure 8:
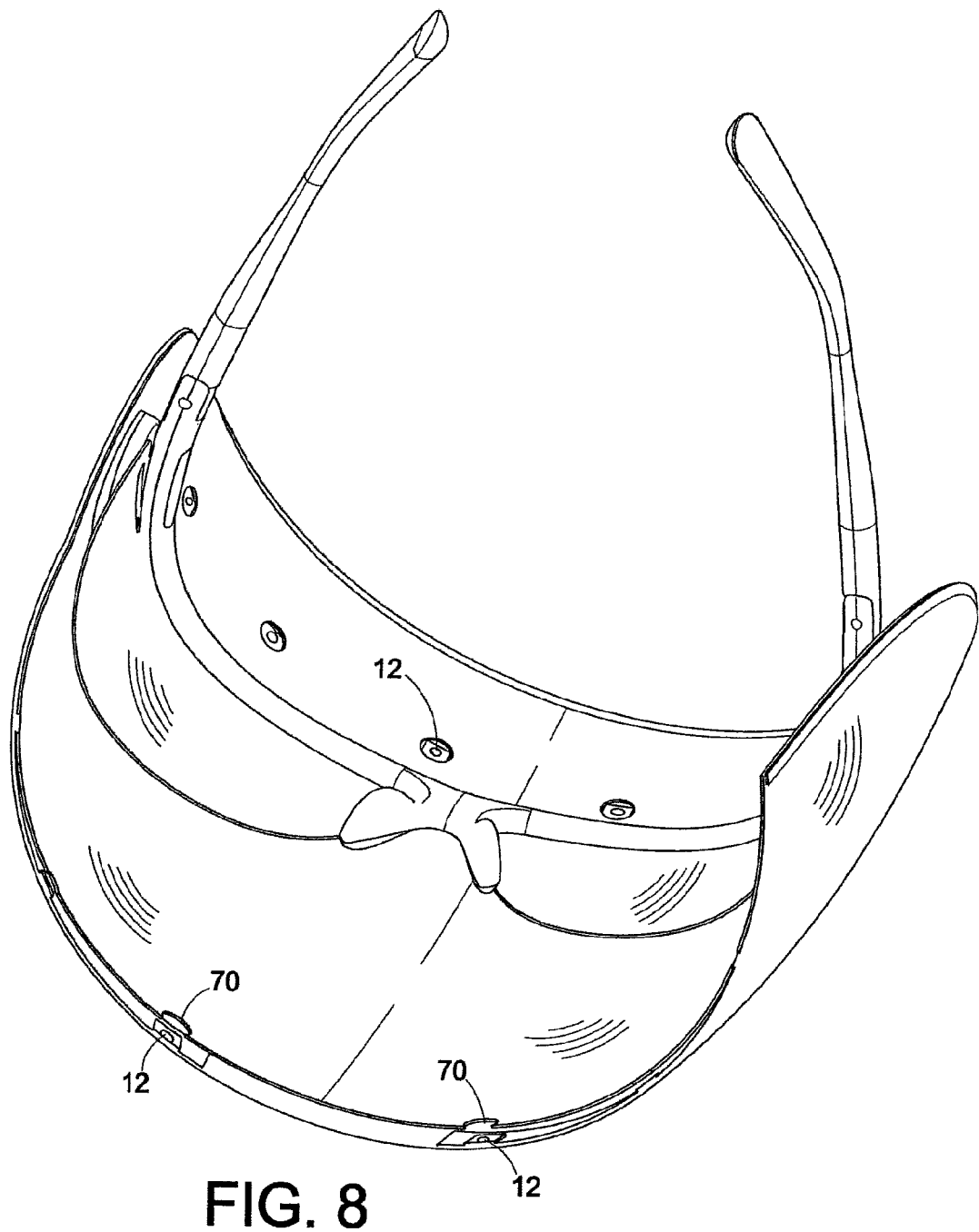
FIG. 8 is a partial cross-sectional perspective view illustrating disposition of recessed LED lamps relative to inner wall apertures.

Battery pack B (FIG. 5) holds the supply batteries 81 and processing controller 82 that is in electrical communication with the lamps through wire 80. The wiring between connectors 83 and LED strips 12 is not shown to avoid drawing clutter but is contained between walls 50, 52. The battery pack will include an on-off switch 84 and a user interface 86. The processing controller 82 may include a variety of control systems indicating device usage to the user. Such a system would be a counter. The user interface may comprise a display for a variety of useful information from the controller control systems to the user, such as a count of the number of times of usage and communication that the device has been used enough times such that the LEDs themselves have degraded and a replacement is recommended for the therapy.

Figure 11:
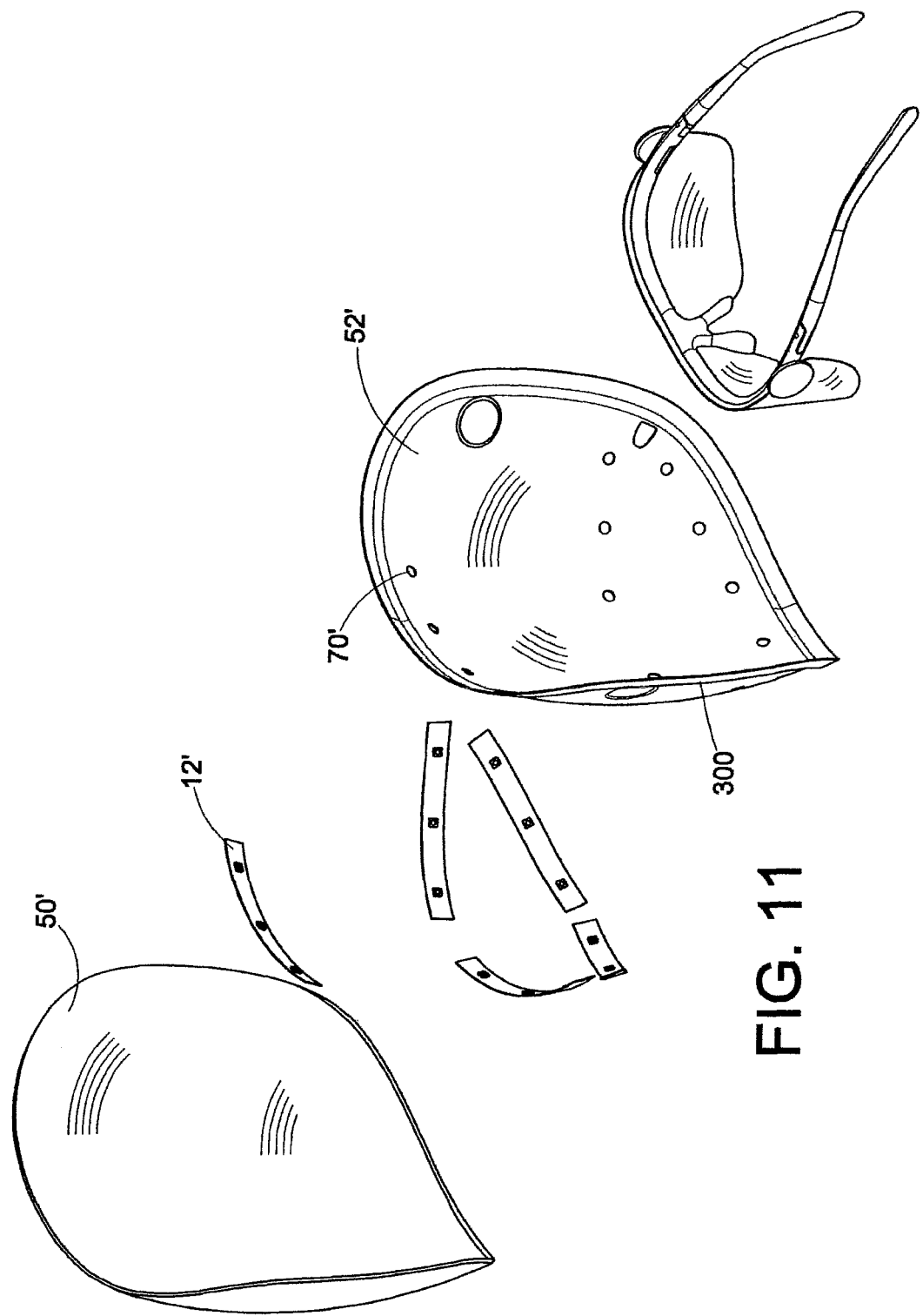
FIG. 11 is an exploded view of an alternative embodiment wherein the mask walls are spaced by a flange.
Figure 12:
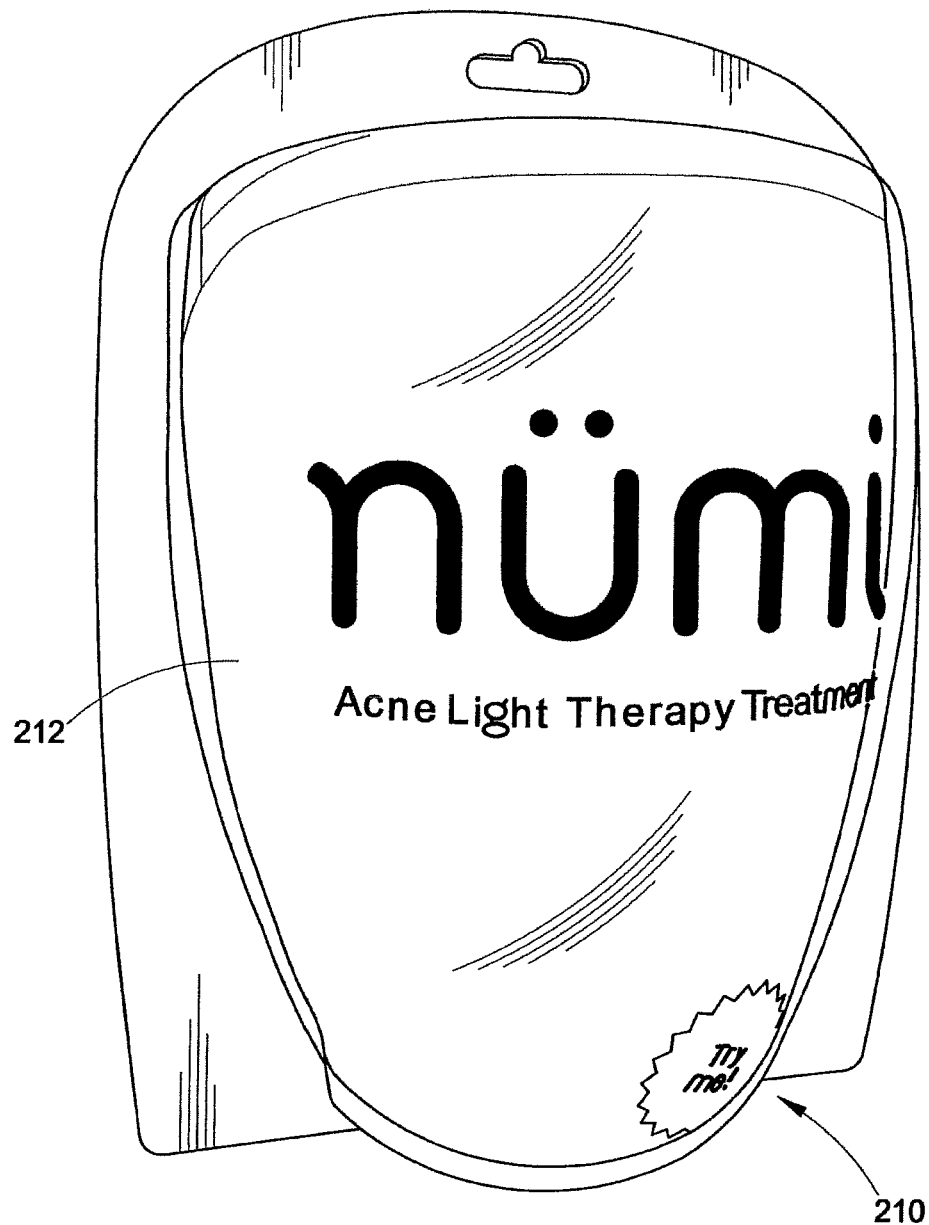
FIG. 12 is an embodiment of a packaging assembly containing the device of FIG. 1.

"Try-me packaging", FIGS. 11 and 12, presents a demonstrative use opportunity to a potential user while still packaged. The subject embodiments further include a packaging assembly 210 containing the device wherein a switch S1 (not shown) for operating the lamp assembly has a multi-position effect functionality including an on-mode, an off-mode and a try-me mode. The try-me mode is accessible while the lamp assembly is contained in packaging for displaying lamp operation to a user. The packaging includes a clear or translucent cover 212 over the device A. A try-me time-out circuit is included for limiting the try-me display time of lamp operation, such as, for example two seconds. Lamp on-time as measured by the counter is segregable from the try-me mode so that try-me usage will not affect dosage count of the device for actual therapy. It is assumed try-me usage time will be negligible relative to a dosage use time.

The subject devices include multiple benefits to the user in a wearable hands-free device with a remote battery pack. The device is properly positionable in a relatively automatic way with minimal human touch by exploiting user reference contact points, and is particularly hand-free during use. No sharp or hot surfaces are engageable by the user. A smooth seamless surface faces the user and is properly spaced from the treatment area to provide enhanced ventilation and minimal discomfort during treatment.

Figure 13:
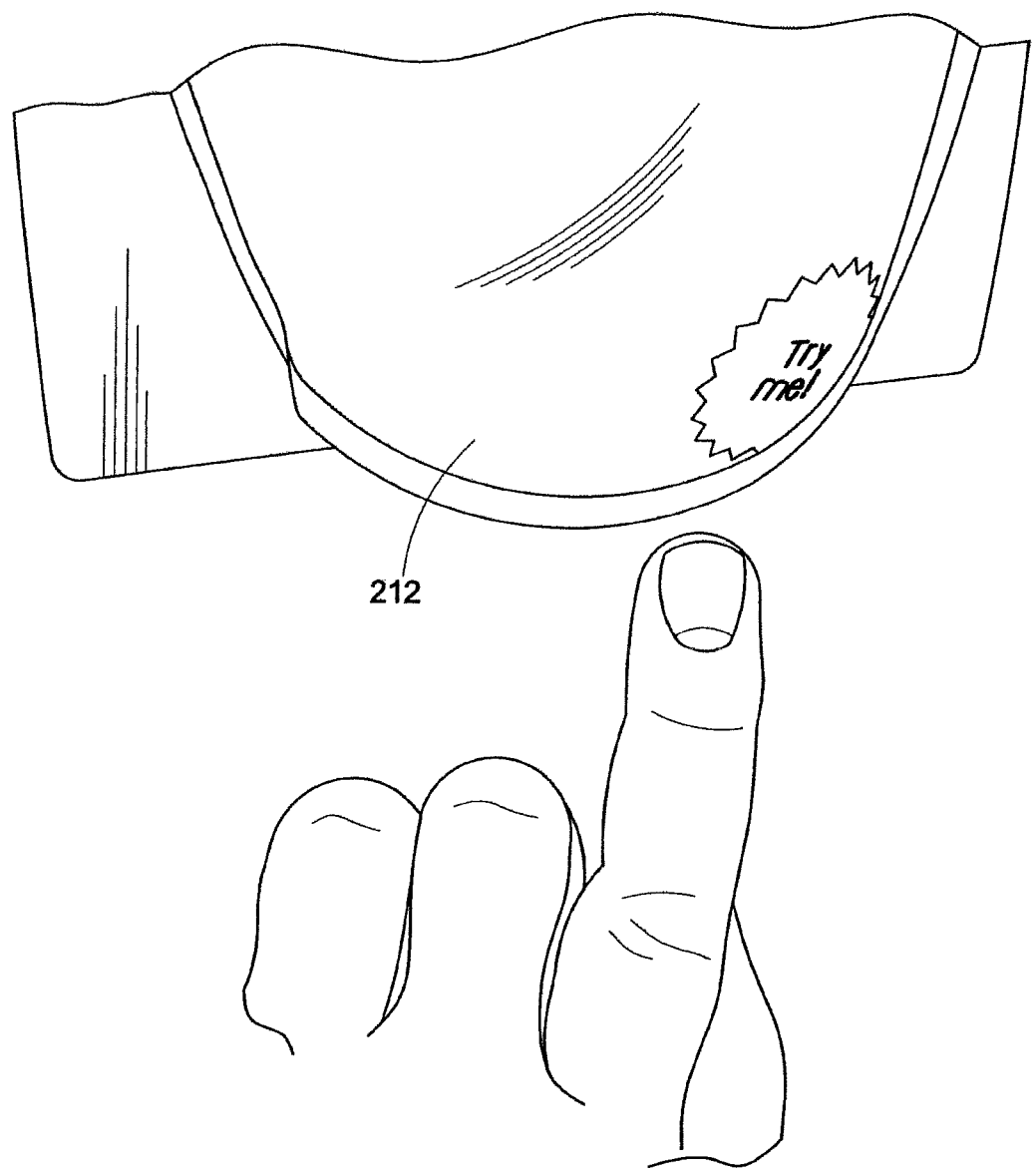
FIG. 13 illustrates a try-me feature of the packaging of FIG. 11 wherein a user can view a sample operation of the device.
Figure 14:
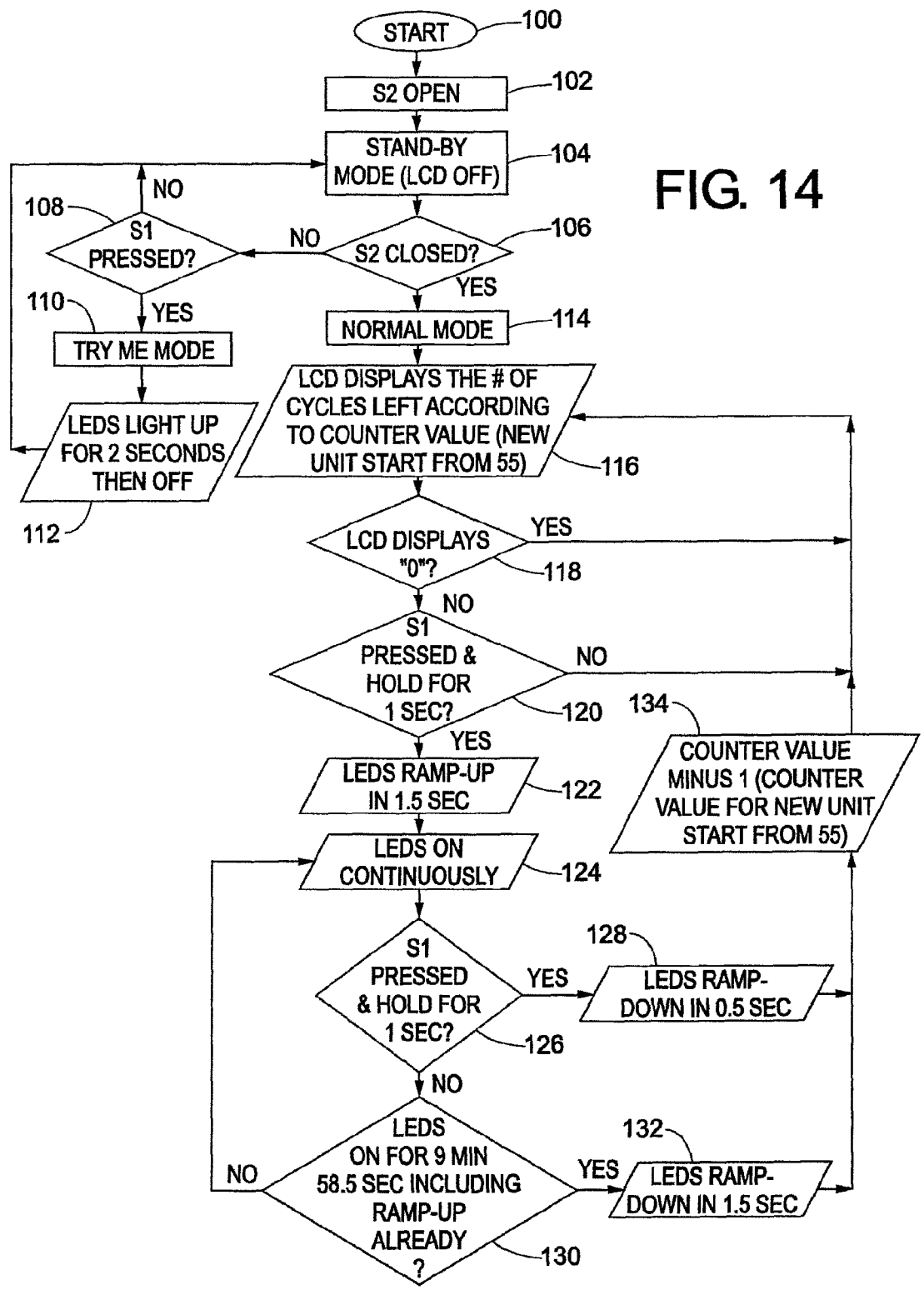
FIG. 14 is a flowchart of operational device control.

With particular reference to FIG. 13, a flowchart illustrating an operational embodiment of a device control is illustrated. The device visioned as operational by FIG. 10 includes two switches, S1, S2, at least one of which are required to be closed to communicate energy from an energy source to the therapeutic lamps. S2 is a safety switch which is open when the device is in sales packaging so that only the "try-me" mode is enabled when S2 is open. After removal from the packaging, S2 can be closed and the device can be operated in a normal mode. Accordingly, after start 100, and in a situation when S2 is opened 102, such as when the device is still within the packaging, the system will remain in a stand-by mode wherein the GUI interface (such as an LCD) is off 104. If S2 remains closed 106 but S1 is pressed 108 (e.g. FIG. 12), then the device can enter the "try-me" mode 110 wherein the LEDs will light up for two seconds, then turn off 112. Such a "try-me" mode operational demonstration to a user while the device is in a packaging communicates to the user actual operation and can assist in a decision to purchase, or have a better understanding of how the device operates. If the device is removed from the packaging, and S2 is closed, the device will enter normal mode 114 wherein the GUI will include an LCD displaying the number of cycles left according to a counter value. Note that counter value 134 is not affected by any try-me sampling operation.

In one embodiment, the unit will count down from 55 to 1, as 55 uses is deemed to be enough to diminish enough LED efficiency from the peak operational mode of LEDs when they are used as the therapeutic radiant lamps. Accordingly, upon a user picking up the device, they will immediately know how many cycles are left for acceptable and recommended operation of the device from 55 more uses all the way down to 0 118. If the display shows a count greater than 0, and the user is interested in a therapy session, the user will turn the unit on by pressing S1 120 wherein the LEDs will ramp up to radiant operation 122 in approximately 1.5 seconds and then will radiate continuously 124 until either the user desires to turn off the unit by again pressing S1 126 so that the LEDs can ramp down 128 or until a therapy session has timed out 130 such as for remaining radiant for approximately ten minutes. After completing an appropriate run time of a therapy session, the LEDs will ramp down 132 and the GUI display to the user will subtract 1 from the counter value 134.

Figure 9:
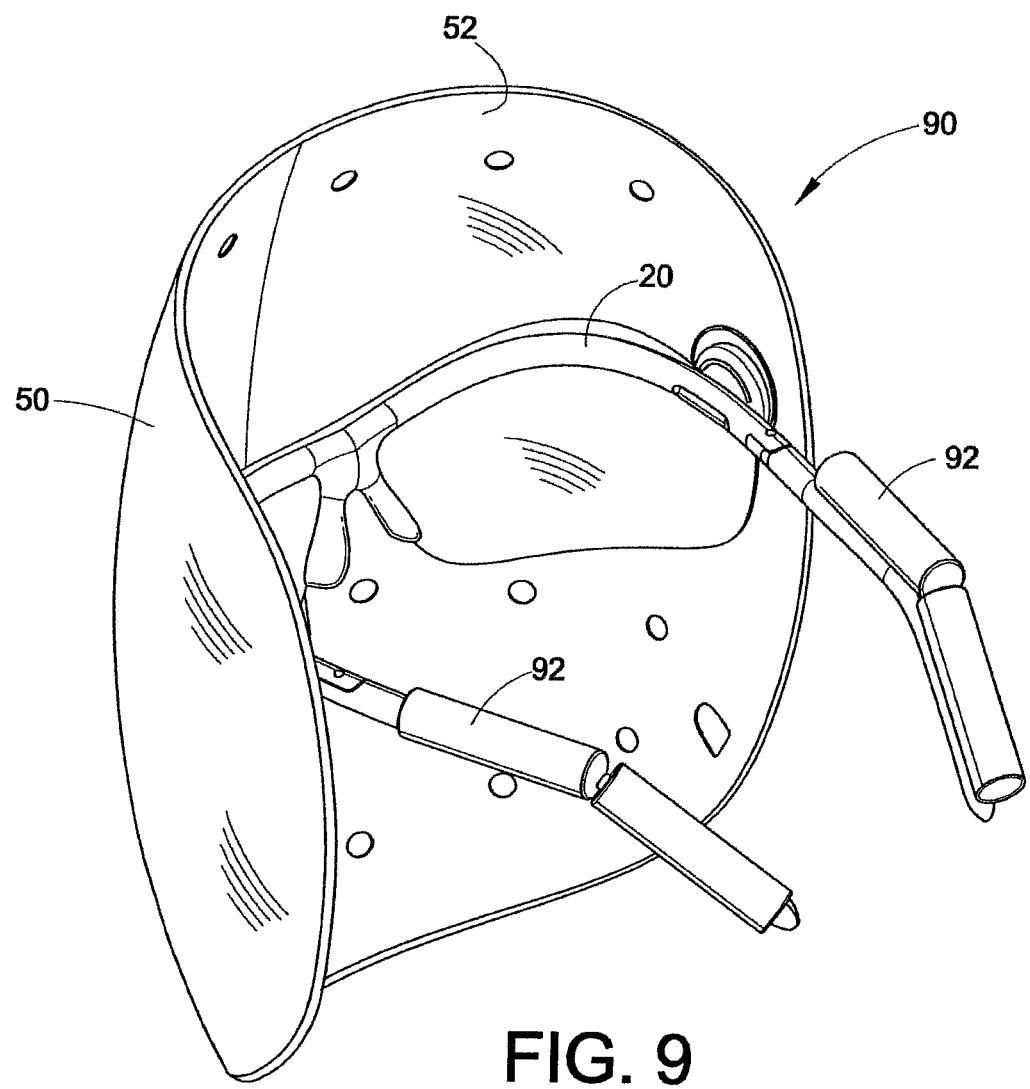
FIG. 9 is a perspective view of an alternative embodiment wherein the power supply and control circuitry are integrally formed with the mask assembly.
Figure 10:
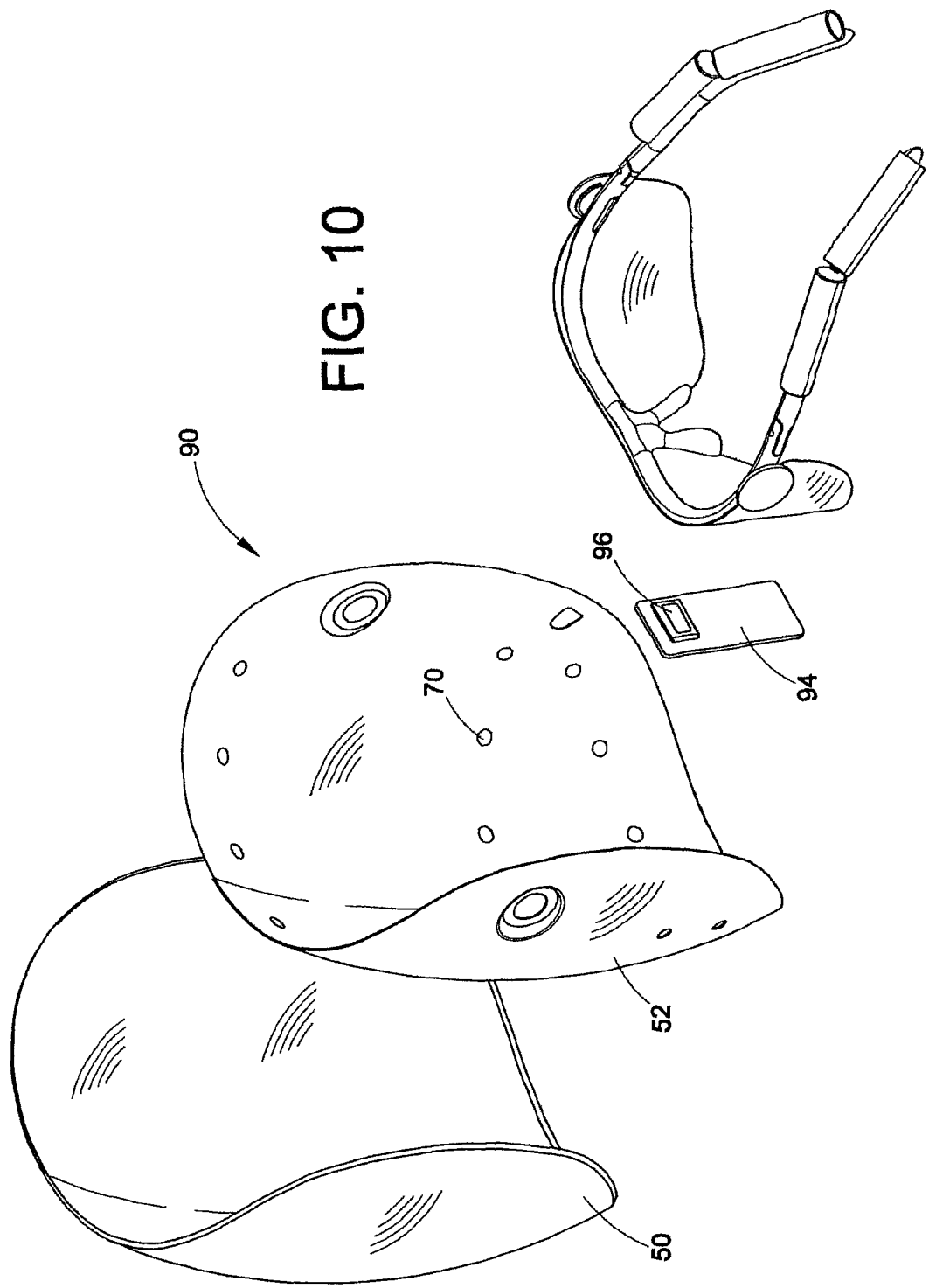
FIG. 10 is an exploded view of the device of FIG. 9.

With reference to FIGS. 9 and 10, an alternative embodiment is shown wherein a controller B is eliminated and the energy source and processing control are all integrally assembled in the device 90. In this case, the platform 20 and walls 50, 52 remain substantially the same as per the FIG. 1 device. However, the energy source such as batteries 92 are disposed as part of the eyeglass temple arms wherein wires provide energy from the batteries 92 to the LEDs through the hinge points of the frame 20 and into the spacing 54 for ultimate connection to the LEDs themselves. The controller 94 including LCD display 96 is also housed behind the reflective wall 52 relative to the user, which wall 52 can include a relatively small cutout (not shown) for the screen 96.

The embodiment of FIGS. 9 and 10 is thus even more compact than the embodiment of FIG. 1, and more hands-free therefrom, as it eliminates the need to somehow manage the controller B during operation.

FIG. 11 shows yet another alternative embodiment wherein the outer wall 50' and the inner wall 52' are not spaced by being configured with different curvatures. Rather, the walls 50', 52' have the same curvature, but the inner wall 52 has an off step 300 depending from the wall perimeter to form a flange raised from the surface of the wall 52' towards the outer wall 50' to effectively form a spacer between the two. In one embodiment, the flange 300 is about 8 millimeters wide, continues around the entire perimeter of the wall 52' and is about 0.5 millimeters thick for effecting the desired spacing between the inner and outer walls. In this embodiment the flange 300 is part of the inner wall 52', and as in the foregoing embodiment, both walls are vacuumed formed plastic, either PET or PVC. The assembly of FIG. 11 can be sonic welded, glued, or adhered with double-sided adhesive. Alternatively, a plurality of intermediate sealing points (not shown) could be used instead of a continuous seal. In this embodiment it can be seen that there is an alternative number of LEDs 12' opposite the forehead portion of the assembly relative to the user so that the number of apertures 70' and LEDs 12' are reduced from the foregoing embodiment from eighteen to fifteen. Either number are viable implementations of the desired therapy, although the other componentry of the assembly FIG. 11 is substantially the same as that shown in the foregoing Figs.

Another alternative embodiment from the device shown in FIG. 1, etc. includes disposition of a transparent flexible polymer sheet (not shown) incorporating working LED lights between outer wall 50 and inner wall 52. Such a configuration would comprise the polymer film being coated with a transparent thin layer of carbon nanotubes in a specific configuration to act as the wire pathways to connect LED lights. The polymer would protect the LEDs from user contact. Such protective polymers are available under the Lumisys brand.

Yet another alternative embodiment includes such a transparent flexible polymer sheet wherein a reflective film is applied on top of the flexible polymer sheet including cutouts opposite the LEDs for allowing the radiant light to communicate through a reflective area in a manner as shown in the relationship of FIG. 4 between the LEDs' 12 inner wall 52 through aperture 70. This arrangement may also include a flexible outer wall 50 on the other side of the flexible polymer sheet to provide malleable rigidity to the film, reflective coating assembly.

Yet another alternative embodiment includes a plurality of sensors (not shown), such as temperature or radiant energy sensors, disposed relative to inner wall 52 to monitor radiant energy exposure of a user during therapy. If such exposure is deemed inappropriate for any reason, sensing thereof is recognized by controller B and the therapy can be halted.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:
1. A phototherapy device comprising:
 a wearable therapeutic lamp platform including a plurality of radiant lamps including a mixed combination of different wavelength radiant energy and a malleable flexible reflective wall optically associated with the radiant lamps and disposed to communicate the radiant energy to a user treatment area, wherein the reflective wall is further formed according to a substantially parabolic bias for dispersing the radiant energy across the user treatment area and reflecting the radiant energy from the user treatment area back to the user treatment area, and wherein upon device receipt on a user the reflective wall parabolic bias expands to a form to match a size of the user treatment area; and a frame for supporting the platform on the user and positioning the therapeutic lamp platform to position the reflective wall towards the user treatment area and to space the reflective wall from the user treatment area at a distance spaced from a nose of the user to provide ventilation and clearance between the reflective wall and the nose of the user, and the frame including an eye shielding lens.

2. The phototherapy device according to claim 1, further comprising an outer wall spaced from the reflective wall and wherein the radiant lamps are interposed between the outer wall and the reflective wall.

3. The phototherapy device according to claim 1, further comprising an outer wall spaced from the reflective wall and wherein at least a portion of the radiant lamps are interposed between the outer wall and the reflective wall.

4. The phototherapy device according to claim 1, further comprising an outer wall spaced from the reflective wall and wherein the lamps are mounted on the outer wall.

5. The phototherapy device according to claim 1, wherein the frame is sized to space the lamp platform from the user treatment area at a desired position for proper therapeutic treatment.

6. The phototherapy device according to claim 1, wherein the frame includes user contact points disposed to guide the lamp platform to the desired position.

7. The phototherapy device according to claim 1, wherein at least a portion of the lamps are recessed relative to the reflective wall.

8. The phototherapy device according to claim 1, wherein the different wavelength radiant energy includes at least two of red, blue and infrared.

9. The phototherapy device according to claim 1, wherein the reflective wall is a smooth and seamless wall towards the user.

10. The phototherapy device according to claim 1, wherein the frame includes an eyeglass frame.

11. The phototherapy device according to claim 1, wherein the support frame includes an eyeglass frame.

12. The phototherapy device according to claim 1, wherein the support frame includes goggles.

13. A phototherapy device comprising:

a wearable therapeutic lamp platform including a plurality of radiant lamps including a mixed combination of different wavelength radiant energy and a malleable flexible reflective wall optically associated with the radiant lamps and disposed to communicate the radiant energy to a user treatment area, wherein the reflective wall is further formed according to a substantially parabolic bias for dispersing the radiant energy across the user treatment area and reflecting the radiant energy from the user treatment area back to the user treatment area, and wherein upon device receipt on a user, the reflective wall parabolic bias expands to a form to match a size of the user treatment area; and a frame for supporting the platform on the user and positioning the therapeutic lamp platform to position the reflective wall towards the user treatment area and to space the reflective wall from of the user treatment area at a distance spaced from a nose of the user to provide ventilation and clearance between the reflective wall and the nose of the user, and the frame including an eye shielding cover.

14. The phototherapy device according to claim 13, further comprising an outer wall spaced from the parabolic bias shaped reflective wall and wherein the radiant lamps are interposed between the outer wall and the parabolic shaped reflective wall.

15. The phototherapy device according to claim 13, wherein the different wavelength radiant energy includes at least two of red, blue and infrared.

16. The phototherapy device according to claim 13, wherein the parabolic bias shaped reflective wall is a smooth and seamless wall towards the user.

17. The phototherapy device according to claim 13, wherein the frame includes an eyeglass frame.

18. The phototherapy device according to claim 13, wherein the frame includes goggles.

* * * * *